United States Patent [19]

Cale, Jr.

[11] Patent Number: 4,746,655
[45] Date of Patent: May 24, 1988

[54] FUSED AROMATIC-SPIROPIPERIDINE OXAZEPINONES(AND THIONES)

[75] Inventor: Albert D. Cale, Jr., Mechanicsville, Va.

[73] Assignee: A. H. Robins Company, Incorporated, Richmond, Va.

[21] Appl. No.: 60,265

[22] Filed: Jun. 10, 1987

[51] Int. Cl.$^4$ .................. A61K 31/55; C07D 267/14; C07D 267/08
[52] U.S. Cl. .................... 314/211; 540/488; 546/193; 546/194; 546/221; 546/242
[58] Field of Search ........................ 540/488; 314/211

[56] References Cited
U.S. PATENT DOCUMENTS
4,592,866 6/1986 Cale, Jr. ............................ 540/488

Primary Examiner—Robert T. Bond

[57] ABSTRACT

Novel aromatic-spiropiperidineoxazepinones and thiones exhibiting antihistamine activity are disclosed having the formula:

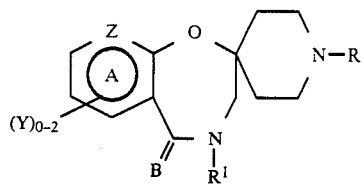

wherein
A represents an aromatic ring, selected from benzo when Z is carbon or pyrido[3,2-f] when Z is nitrogen either of which rings may be optionally substituted on carbon;
B is selected from oxygen or sulfur;
$R^1$ is selected from the group consisting of loweralkyl, cycloalkyl, cycloalkyl-loweralkyl or phenyl-loweralkyl of which phenyl may be optionally substituted;
R is selected from the group consisting of loweralkyl, cycloalkyl or phenyl-loweralkyl of which phenyl may be optionally substituted and the pharmaceutically acceptable salts thereof and novel chemical intermediates in the preparation thereof.

12 Claims, No Drawings

FUSED AROMATIC-SPIROPIPERIDINE OXAZEPINONES(AND THIONES)

BACKGROUND OF THE INVENTION

1. Field of Invention

The present invention is concerned with 1,4'-disubstituted spiro[piperidine-4,2'(3'H)-aromatic-1,4-oxazepine]-5'(4'H)-ones and thiones and is more particularly concerned with compounds wherein the aromatic moiety is benzo or pyrido[3,2-f], the compounds having antihistaminic utility in a living animal body, and a novel process and novel intermediates for the preparation thereof.

2. Information Disclosure Statement

Fused aromatic oxazepinones (and thiones) having an amino alkyl radical at the same junction with the aromatic-1,4-oxazepine moiety as that of the spiro formation in the present invention, i.e., the 2-position, are disclosed in U.S. Pat. No. 4,592,866. The compounds also have antihistaminic activity in a living animal body.

OBJECTS AND SUMMARY OF THE INVENTION

The novel aromatic-spiropiperdine oxazepinones and thiones of the present invention have the composite formula:

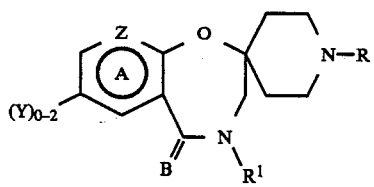

Formula I wherein;

A represents an aromatic ring, having two of its carbon atoms held mutually with the ozazepine moiety, selected from benzo when Z is carbon or pyrido[3,2-f] when Z is nitrogen, either of which rings may be optionally substituted on carbon by one or two radicals selected from the group consisting of nitro, halo, loweralkyl, loweralkoxy, diloweralkylamino, amino, phenyl, or trifluoromethyl;

B is selected from oxygen or sulfur;

$R^1$ is selected from the group consisting of loweralkyl, cycloalkyl, cycloalkyl-loweralkyl or phenyl-loweralkyl of which phenyl may be optionally substituted by one to three radicals selected from halo, loweralkyl, loweralkoxy, nitro or trifluoromethyl;

R is selected from the group consisting of loweralkyl, cycloalkyl, or phenyl-loweralkyl of which phenyl may be optionally substituted by one to three radicals selected from loweralkyl, loweralkoxy, or trifluoromethyl and the pharmaceutically acceptable acid addition salts thereof.

Certain novel chemical intermediates have the formula:

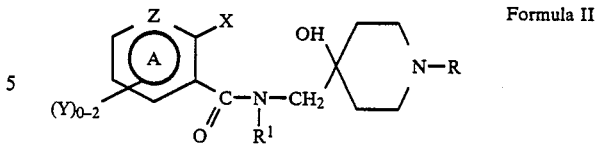

Formula II wherein Z is selected from nitrogen, forming a pyridine "A" ring, or from carbon, forming a benzene "A" ring, either of which rings may be optionally substituted on carbon by one or two Y radicals selected from the group consisting of nitro, halo, loweralkyl, loweralkoxy, diloweralkylamino or trifluoromethyl; R and $R^1$ are as defined under Formula I and X is halo (Cl, Br, F or I) when A is a pyridine ring and X is limited to fluoro when A is a benzene ring, except when Y is a nitro group ortho or para to X in which case X may also be chloro or bromo.

In the further definition of symbols in the formulas hereof and where they appear elsewhere throughout this specification and the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec. butyl, tert. butyl, amyl, isoamyl, hexyl, heptyl and octyl radicals and the like. The term "loweralkoxy" has the formula —O— loweralkyl.

The term "cycloalkyl" as used herein includes primarily cyclic alkyl radicals containing 3–9 carbon atoms inclusive and includes such radicals as cyclopropyl, cyclobutyl, cyclopentyl, cyclohexyl, methylcyclohexyl, cycloheptyl and the like.

The terms "halo" or "halogen" when referred to herein include fluorine, chlorine, bromine and iodine unless otherwise stated.

"Pharmaceutically acceptable salts" include acid addition salts, hydrates, alcoholates and quarternary salts of the compounds of Formula I which are physiologically compatible in warm-blooded animals. The acid addition salts may be formed by either strong or weak acids. Representative of strong acids are hydrochloric, sulfuric and phosphoric acids. Representative of weak acids are fumaric, maleic, succinic, oxalic, citric, tartaric, hexamic and the like. The free bases of the salts may be obtained by partitioning the salt in an organic solvent aqueous basic mixture and separating the organic layer and evaporating the solvent therefrom.

Suitable quarternary salts include the loweralkyl halides and loweralkyl sulfates.

By "sulfurizing agent" is meant any agent or mixture of agents which will convert oxazepinones to oxazepine-thiones such as 2,4-bis(4-methoxyphenyl)-1,3,2,4-dithiadiphosphetane-2,4-disulfide (Lawesson reagent) or a mixture of phosphorus pentasulfide and alkali metal sulfide or a mixture of phosphorus pentasulfide in a suitable solvent such as acetonitrile, toluene or pyridine. By the use of "sulfurizing agent" the oxazepinones are thereby "sulfurized" to oxazepine-thiones.

The compounds of Formula I of the present invention exhibit antihistaminic activity in guinea pigs. The method of testing is a modification of the procedure of Tozzi et al. (Agents and Actions, Vol. 4/4, 264–270, 1974) as follows:

Guinea pigs are fasted 18–24 hr in individual cages. Water is available ad libitum. On the test day, animals in groups of 3 are injected intraperitoneally with 30 mg/kg of the test compound prepared in an appropriate vehicle. Thirty minutes later histamine at a dosage level of 1.2 mg/kg (=2×the $LD_{99}$) is injected into a marginal ear vein. Survival of the guinea pigs for 24 hr is positive evidence of antihistaminic activity and of ability to counteract histamine in a living animal body. If the vehicle used for the test compound is other than water, its effect is established by testing an equal amount as control. The dose protecting 50% of the animals ($PD_{50}$) from death may be established from dose-response curves.

The process for preparing compounds of Formulas I and II comprises the steps of Step 1, reacting a compound having the formula:

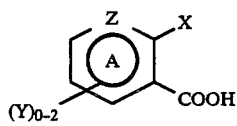

and a compound having the formula:

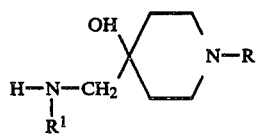

wherein Y, Z, R and $R^1$ are defined under Formula I and X is as defined under Formula II above, in succession with hydroxybenzotriazole hydrate and 1,3-dicyclohexylcarbodiimide in a suitable solvent, e.g., methylene chloride to give a compound having the formula:

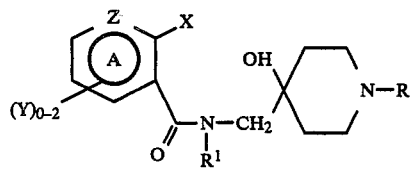

Formula II wherein the symbols are as defined above;

Step 2, reacting the compound prepared in step 1 with a strong base such as sodium hydride in a suitable solvent, e.g., dimethylsulfoxide to give a compound having the formula

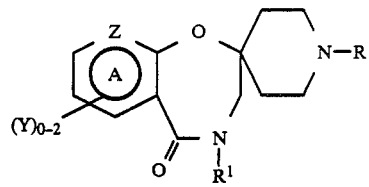

wherein the symbols are as defined under Formula I, and Step 3 optionally sulfurizing a compound prepared in Step 2 to give a compound having the formula:

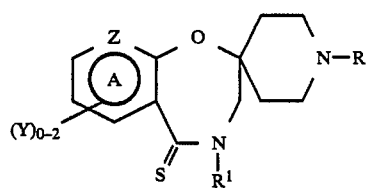

DETAILED DESCRIPTION OF THE INVENTION

Chart 1 depicts the various methods of preparing starting 4-aminomethyl-1-substituted-4-piperidinol and the use thereof in the process for preparing compounds of Formula I described hereinabove.

Compounds of Formula I, wherein the aromatic A ring is pyrido[3,2-f] optionally substituted by one or two Y groups are preferred for their counteracting effect on histamine in a living animal body.

CHART 1

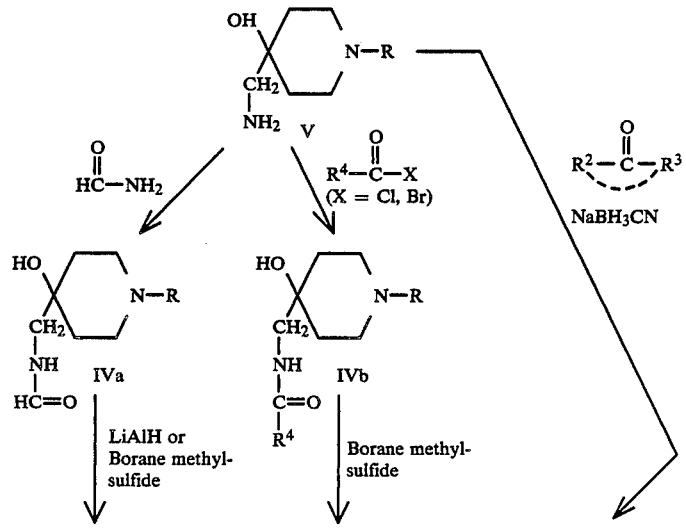

CHART 1

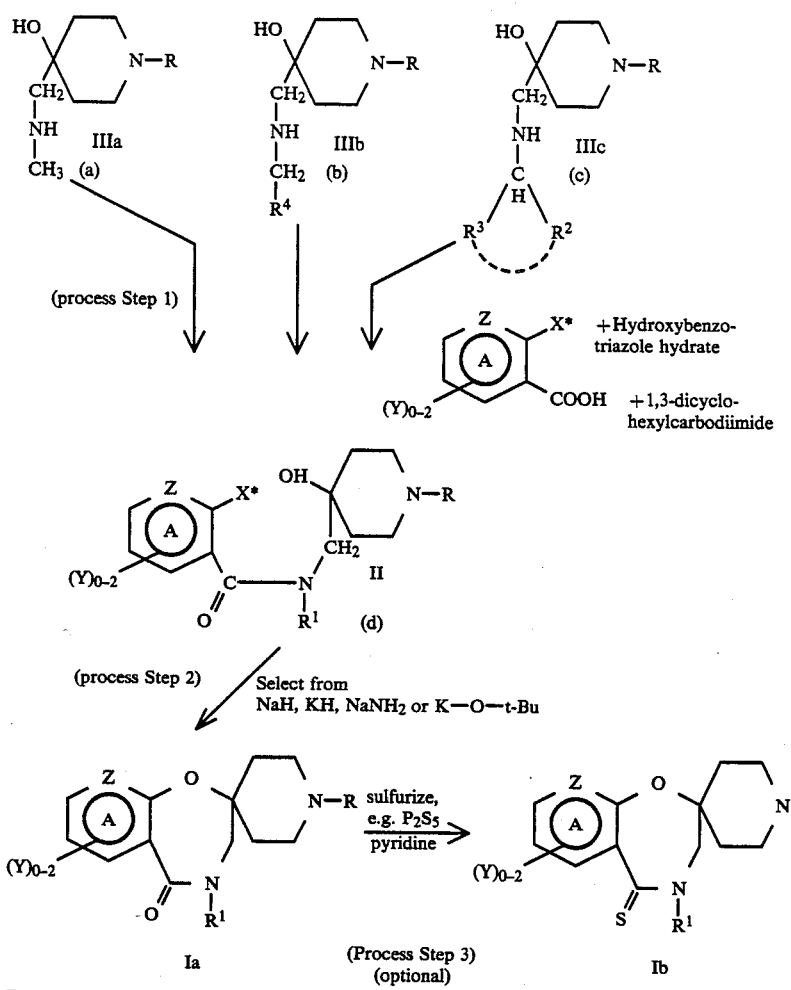

Footnotes to Chart 1
*X is as defined under Formula II above.
(a) $R^1$ is methyl.
(b) $R^4$—$CH_2$— becomes $R^1$ excluding methyl and may be loweralkyl above methyl (i.e., $C_2$–$C_8$), phenyl-loweralkyl or cycloalkyl-loweralkyl.

(c) $R^1$ is 

and may form loweralkyl ($C_1$–$C_8$), phenyl-loweralkyl of cycloalkyl
(d) $R^1$ is a composite of values given for $R^1$ under Formula I.

Chart 2 illustrates by equation an alternate method of preparing 7'-chloropyrido-spiropiperidineoxazepinones.

Chart II

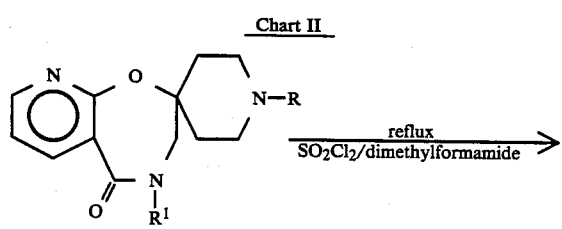

-continued
Chart II

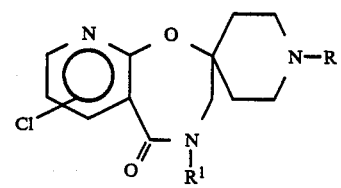

Chart 3 illustrates by equation the preparation of starting 4-(aminomethyl)-1-substituted-4-piperidinol compounds of Formula V (see Chart 1).

Chart 3

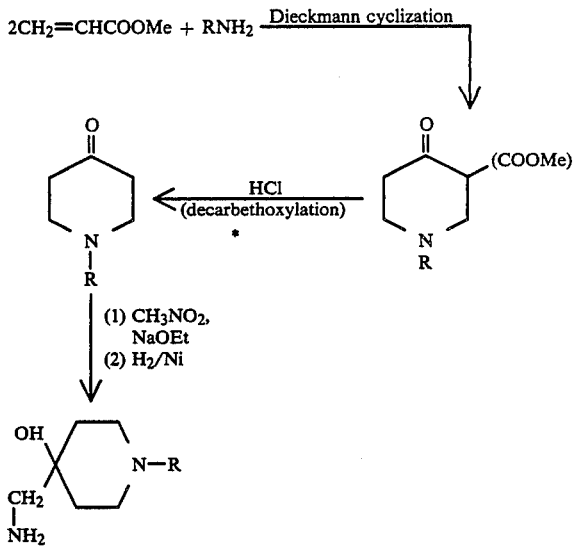

*See C.A. 84, 17157p for preparation of N—benzyl-4-piperidones and C.A. 71, 38844g for preparation of 1-alkyl-4-piperidones. 1-Methyl-4-piperidone is available commercially.

Compounds of Formula I wherein Y is amino may be prepared from compounds of Formula I wherein Y is nitro by reducing the nitro substituted compound with ammonium sulfide in water (~23%) and in ethanol solvent. The reaction mixture is typically heated at reflux for approximately 4-8 hr. After cooling, the reaction mixture is acidified and ethanol solvent removed to give a residue which is made basic. Partitioning between an aqueous and organic phase gives the desired compound as a free base. The nitro compound may also be reduced with Raney nickel and hydrogen to give the amino compound.

Compounds of Formula I wherein Y is diloweralkylamino may be prepared from compounds of Formula I wherein Y is halo by reaction of the halo substituted compound with the desired diloweralkylamine compound in a stainless steel bomb at about 100° C. for about 12 to 24 hr. After cooling the bomb is opened, and the diloweralkylamine evaporated to give a residue. The residue is dissolved in an appropriate organic solvent, e.g., chloroform and washed with a basic aqueous solution such as dilute soduim hydroxide solution. The organic layer is dried, and concentrated to give the desired compound as a free base.

The preparations illustrate methods of preparing the 4-(aminomethyl)-1-substituted-4-piperidinols and the intermediates illustrate preparation of the pyridine and benzene carboxamide chemical intermediates of Formula II. The examples illustrate the preparation of Formula I compounds. The intermediates and examples taken together illustrate the process. The products of the examples are illustrated by structure symbols in Table 1. The scope of the invention is not limited by the preparations, intermediates and examples, however.

PREPARATION 1

4-(Aminomethyl)-1-methyl-4-piperidinol acetate [1:1].

To a solution of sodium ethoxide prepared by dissolving 23 g (1 mole) of sodium in 1500 ml of ethanol was added dropwise a mixture of 113 g (1 mole) of 1-methyl-4-piperidinone and 75 g (1.3 mole) of nitromethane at a rate so as to maintain a temperature (preheated) of 50° C. The solution was stirred for 4 hr and 150 g of acetic acid was added dropwise. The mixture was filtered and the filtrate was concentrated. The residue was crystallized from ethyl acetate. The resulting solid was dissolved in 1 liter of ethanol and treated with 2 teaspoonsful of Raney nickel catalyst. The mixture was hydrogenated for 3 hr at ambient temperature. The residue was crystallized from acetonitrile. Yield of title compound was 80 g (39%).

A 10 g sample was recrystallized from the same solvent to give 9 g of crystals, m.p. 123°-125° C.

Analysis: Calculated for $C_9H_{28}N_2O_3$: C, 52.92; H, 9.86; N, 13.71; Found: C, 52.58; H, 9.92; N, 13.54.

PREPARATION 2

N-(4-Hydroxy-1-methyl-4-piperidinylmethyl)formamide.

A mixture of 50 g (0.35 mole) of 4(aminomethyl)-1-methyl-4-piperidinol and 15.8 g (0.35 mole) of formamide was stirred at 145° C. for 6 hr and allowed to stand overnight. The mass spectra indicated the starting amine was still present. The reaction mixture was reheated to 160° C. and stirred for 1 hr. The heat was removed and 150 ml of toluene was added. On cooling 61 g of crystals were formed, m.p. 116°-122° C. A 5 g sample was recrystallized from toluene to give 4.2 g of the title compound, m.p. 122°-124° C.

Analysis: Calculated for $C_8H_{16}N_2O_2$: C, 55.79; H, 9.36; N, 16.26; Found: C, 55.77; H, 9.40; N, 16.19.

PREPARATION 3

1-Methyl-4-[(methylamino)methyl]-4-piperidinol oxalate [1:2].

A mixture of 46 g (0.23 mole) of 4-(aminomethyl)-1-methyl-4-piperidinol acetate [1:1] and 10.2 g (0.23 mole) of formamide was stirred at 160° C. until evolution of ammonia ceased (about 24 hr). The reaction mixture was dissolved in 150 ml of tetrahydrofuran and treated dropwise at reflux with 101 ml (1.01 mole) of 10M borane-methylsufide. Reflux was continued for 5.5 hr and the mixture was allowed to stand at room temperature over the weekend. Approximately 200 ml of methanol was added dropwise and the mixture was heated to reflux for 1 hr. Hydrogen chloride gas was bubbled into the mixture until a pH of <1 persisted. The mixture was heated to reflux for 3 hr and filtered. The filtrate was treated with 500 ml of dilute sodium hydroxide and extracted 4 times with ether. The aqueous layer was continuously extracted with chloroform for 24 hr. The chloroform was concentrated to give 22 g of residue. A 20 g sample was dissolved in 80 ml of ethanol. The resulting crystals were recrystallized from methanol-water to give 15 g of crystals, m.p. 197°-199° C.

Analysis: Calculated for $C_{12}H_{22}N_2O_9$: C, 42.60; H, 6.55; N, 8.28; Found: C, 43.02; H, 6.76; N, 8.49.

PREPARATION 4

1-Methyl-4-[(methylamino)methyl]-4-piperidinol oxalate[1:2].

N-(4-Hydroxy-1-methyl-4-piperidinylmethyl)formamide, 86 g (0.5 mole) was added to a stirred suspension of 28.5 g (0.75 mole) of lithium aluminum hydride in 1500 ml of tetrahydrofuran over a 20 min period. The mixture was heated to reflux for 20 hr with continued stirring. The mixture was cooled to 10° C. with an ice bath and a solution of 10 g of sodium hydroxide in 67.5 ml of water added dropwise while cooling. The mixture was filtered and the filtrate was concentrated on a rotary evaporator to give 73 g (92%) residue which crystallized on cooling. The NMR matched that of the compound of Example 3 and appeared to be pure.

PREPARATION 5

Following the procedure of Preparation 2 and substituting the following for 4-(aminomethyl)-1-methyl-4-piperidinol:
(a) 4-(aminomethyl)-1-ethyl-4-piperidinol,
(b) 4-(aminomethyl)-1-cyclohexyl-4-piperidinol,
(c) 4-(aminomethyl)-1-phenylmethyl-4-piperidinol,
(d) 4-(aminomethyl)-1-phenylethyl-4-piperidinol,
(e) 4-(aminomethyl)-1-[(4-methylphenyl)-methyl]-4-piperidinol,
(f) 4-(aminomethyl)-1-[(2-methoxyphenyl)methyl]-4-piperidinol,
(g) 4-(aminomethyl)-1-[(3,4,5-trimethoxyphenyl)methyl]-4-piperidinol, and
(h) 4-(aminomethyl)-1-[(3-trifluoromethylphenyl)methyl]-4-piperidinol
there are obtained:
(a) N-(4-hydroxy-1-ethyl-4-piperidinylmethyl)formamide,
(b) N-(4-hydroxy-1-cyclohexyl-4-piperidinylmethyl)formamide,
(c) N-(4-hydroxy-1-phenylmethyl-4-piperidinylmethyl)formamide,
(d) N-(4-hydroxy-1-phenylethyl-4-piperidinylmethyl)formamide,
(e) N-(4-hydroxy-1-(4-methylphenylmethyl)-4-piperidinylmethyl]formamide,
(f) N-(4-hydroxy-1-(2-methoxyphenylmethyl)-4-piperidinylmethyl]formamide,
(g) N-(4-hydroxy-1-(3,4,5-trimethoxyphenylmethyl)-4-piperidinylmethyl]formamide, and
(h) N-[4-hydroxy-1-(3-trifluoromethylphenylmethyl)-4-piperidinylmethyl]-formamide.

PREPARATION 6

Following the procedure of Preparation 4 and substituting the compounds obtained in Preparation 5 for N-(4-hydroxy-1-methyl-4-piperidinylmethyl)formamide there are obtained:
(a) 1-ethyl-4-[(methylamino)methyl]-4-piperidonol oxalate,
(b) 1-cyclohexyl-4-[(methylamino)methyl]-4-piperidinol oxalate,
(c) 1-phenylmethyl-4-[(methylyamino)methyl]-4-piperidinol oxlate,
(d) 1-phenylethyl-4-[(methylamino)methyl]-4-piperidinol oxalate,
(e) 1-(4-methylphenylmethyl)-4-[(methylamino)methyl]-4-piperidinol oxalate,
(f) 1-(2-methoxyphenylmethyl)-4-[(methylamino)methyl]-4-piperidinol oxalate,
(g) 1-(3,4,5-trimethoxyphenylmethyl)-4-[(methylamino)methyl]-4-piperidinol oxalate and
(h) 1-(3-trifluoromethylphenylmethyl)-4-[(methylamino)methyl]-4-piperidinol oxalate.

PREPARATION 7

1-Methyl-4-phenacylaminomethyl-4-piperidinol and other acyl derivatives 4-(Aminomethyl)-1-methyl-4-piperidinol and benzoyl chloride are reacted in a suitable solvent to give the title compound. Similarly by substituting the following for benzoyl chloride:
(a) acetylchloride,
(b) 4-chlorobenzoyl chloride,
(c) 4-methylbenzoyl chloride, and
(d) cyclohexanecarbonyl chloride
there are obtained:
(a) 1-methyl-4-acetylaminomethyl-4-piperidinol,
(b) 1-methyl-4-(4-chlorophenacylaminomethyl)-4-piperidinol,
(c) 1-methyl-4-(4-methylphenacylaminomethyl)-4-piperidinol, and
(d) 1-methyl-4-(cyclohexanecarbonylaminomethyl)-4-piperidinol.

PREPARATION 8

When the following:
(a) 1-methyl-4-phenacylaminomethyl-4-piperidinol,
(b) 1-methyl-4-acetylaminomethyl-4-piperidinol,
(c) 1-methyl-4-(4-chlorophenacylaminomethyl)-4-piperidinol,
(d) 1-methyl-4-(4-methylphenacylaminomethyl)-4-piperidinol and
(e) 1-methyl-4-(cyclohexanecarbonylaminomethyl)-4-piperidinol,
are reacted with boranemethylsulfide the following are obtained:
(a) 1-methyl-4-[(phenylmethylamino)methyl]-4-piperidinol,
(b) 1-methyl-4-[(ethylamino)methyl]-4-piperidinol,
(c) 1-methyl-4-[(4-chlorophenylmethylamino)methyl]-4-piperidinol,
(d) 1-methyl-4-[(4-methylphenylmethylamino)methyl]-4-piperidinol, and
(e) 1-methyl-4-[(4-cyclohexylmethylamino)methyl]-4-piperidinol.

PREPARATION 9

When 4-(aminomethyl)-1-methyl-4-piperidinol is reacted with the following ketones and sodium cyanoborohydride:
acetone, and
cyclohexanone
the following are obtained:
1-methyl-4-[(isopropylamino)methyl]-4-piperidinol, and
1-methyl-4-[(cyclohexylamino)methyl]-4-piperidinol.

INTERMEDIATE 1

2-Chloro-N-(4-hydroxy-1-methyl-4-piperidinylmethyl)-N-methyl-3-pyridinecarboxamide The following compounds were added to 1500 ml of methylene chloride in the order listed:
(1) 73 g (0.46 mole) 1-methyl-4-[(methylamino)methyl]-4-piperidinol,
(2) 73 g (0.46 mole) 2-chloronicotinic acid,
(3) 62 g (0.46 mole) 1-hydroxybenzotriazole hydrate, and
(4) 94.8 g (0.46 mole) 1,3-dicyclohexylcarbodiimide (DCC).

On addition of the DCC slight cooling was required to maintain a temperature of 25°–30° C. The mixture was stirred 5 hr and filtered. The filtrate was extracted with dilute sodium hydroxide, dried over anhydrous sodium sulfate and concentrated. The residue was crystallized from toluene. Yield of title compound was 102 g (74%), m.p. 125°–128° C.

Analysis: Calculated for $C_{14}H_{20}ClN_3O_2$: C, 56.47; H, 6.77; N, 14.11; Found: C, 56.80; H, 6.96; N, 14.04.

INTERMEDIATE 2

Following the procedure of Intermediate 1 and substituting the following for 1-methyl-4-[(methylamino)methyl]-4-piperidinol:
(a) 1-ethyl-4-[(methylamino)methyl]-4-piperidinol,
(b) 1-cyclohexyl-4-[(methylamino)methyl]-4-piperidinol,
(c) 1-phenylmethyl-4-[(methylamino)methyl]-4-piperidinol,
(d) 1-phenylethyl-4-[(methylamino)methyl]-4-piperidinol,
(e) 1-(4-methylphenylmethyl)-4-[(methylamino)methyl]-4-piperidinol,
(f) 1-(2-methoxyphenylmethyl)-4-[(4-methylamino)methyl]-4-piperidinol,
(g) 1-(3,4,5-trimethoxyphenylmethyl)-4-[(methylamino)methyl]-4-piperidinol,
(h) 1-(3-trifluoromethylphenylmethyl)-4-[(methylamino)methyl]-4-piperidinol
(i) 1-methyl-4-[(phenylmethylamino)methyl]-4-piperidinol,
(j) 1-methyl-4-[(ethylamino)methyl]-4-piperidinol,
(k) 1-methyl-4-[(4-chlorophenylmethylamino)methyl]-4-piperidinol,
(l) 1-methyl-4-[(4-methylphenylmethylamino)methyl]-4-piperidinol,
(m) 1-methyl-4-[[(cyclohexylmethyl)amino]methyl]-4-piperidinol,
(n) 1-methyl-4-[(isopropylamino)methyl]-4-piperidinol, and
(o) 1-methyl-4-[(cyclohexylamino)methyl]-4-piperidinol
there are obtained:
(a) 2-chloro-N-(4-hydroxy-1-ethyl-4-piperidinylmethyl)-N-methyl-3-pyridinecarboxamide,
(b) 2-chloro-N-(4-hydroxy-1-cyclohexyl-4-piperidinylmethyl)-N-methyl-3-pyridinecarboxamide,
(c) 2-chloro-N-(4-hydroxy-1-phenylmethyl-4-piperidinylmethyl)-N-methyl-3-pyridinecarboxamide,
(d) 2-chloro-N-(4-hydroxy-1-phenylethyl-4-piperidinylmethyl)-N-methyl-3-pyridinecarboxamide,
(e) 2-chloro-N-[4-hydroxy-1-(4-methylphenylmethyl)-4-piperidinylmethyl]-N-methyl-3-pyridinecarboxamide,
(f) 2-chloro-N-[4-hydroxy-1-(4-methoxyphenylmethyl)-4-piperidinylmethyl]-N-methyl-3-pyridinecarboxamide,
(g) 2-chloro-N-[4-hydroxy-1-(3,4,5-trimethoxyphenylmethyl)-4-piperidinylmethyl]-N-methyl-3-pyridinecarboxamide,
(h) 2-chloro-N-[4-hydroxy-1-(3-trifluoromethylphenylmethyl)-4-piperidinylmethyl]-N-methyl-3-pyridinecarboxamide,
(i) 2-chloro-N-(4-hydroxy-1-methyl-4-piperidinylmethyl)-N-(phenyl methyl)-3-pyridinecarboxamide,
(j) 2-chloro-N-(4-hydroxy-1-methyl-4-piperidinylmethyl)-N-ethyl-3-pyridinecarboxamide,
(k) 2-chloro-N-(4-hydroxy-1-methyl-4-piperidinylmethyl)-N-(4-chloro phenylmethyl)-3-pyridinecarboxamide,
(l) 2-chloro-N-(4-hydroxy-1-methyl-4-piperidinylmethyl)-N-(4-methylphenylmethyl)-3-pyridinecarboxamide,
(m) 2-chloro-N-(4-hydroxy-1-methyl-4-piperidinylmethyl)-N-(cyclohexylmethyl)-3-pyridinecarboxamide,
(n) 2-chloro-N-(4-hydroxy-1-methyl-4-piperidinylmethyl)-N-isopropyl-3-pyridine carboxamide, and
(o) 2-chloro-N-(4-hydroxy-1-methyl-4-piperidinylmethyl)-N-cyclohexyl-3-pyridinecarboxamide.

INTERMEDIATE 3

2-Fluoro-N-(4-hydroxy-1-methyl-4-piperidinylmethyl)-N-methylbenzamide

Following the procedure of Intermediate 1, the following are reacted in the order listed:
(1) 1-methyl-4-[(methylamino)methyl]-4-piperidinol,
(2) 2-fluorobenzoic acid,
(3) 1-hydroxybenzotriazole hydrate, and
(4) 1,3-dicyclohexylcarbodiimide, to give the title compound.

INTERMEDIATE 4

Following the procedure of Intermediate 3 and substituting the following for 2-fluorobenzoic acid:
(a) 5-chloro-2-fluorobenzoic acid,
(b) 4-chloro-2-fluorobenzoic acid,
(c) 5-bromo-2-fluorobenzoic acid,
(d) 2-fluoro-5-methylbenzoic acid, and
(e) 2-fluoro-5-methoxybenzoic acid
there are obtained:
(a) 5-chloro-2-fluoro-N-(4-hydroxy-1-methyl-4-piperidinylmethyl)-N-methylbenzamide,
(b) 4-chloro-2-fluoro-N-(4-hydroxy-1-methyl-4-piperidinylmethyl)-N-methylbenzamide,
(c) 5-bromo-2-fluoro-N-(4-hydroxy-1-methyl-4-piperidinylmethyl)-N-methylbenzamide,
(d) 2-fluoro-5-methyl-N-(4-hydroxy-1-methyl-4-piperidinylmethyl)-N-methylbenzamide, and
(e) 2-fluoro-5-methoxy-N-(4-hydroxy-1-methyl-4-piperidinylmethyl)-N-methylbenzamide.

INTERMEDIATE 5

Following the procedure of Intermediate 1 and substituting the following for 2-chloronicotinic acid:
(a) 5-bromo-2-chloro-4-pyridinecarboxylic acid
(b) 2-chloro-5-methyl-3-pyridinecarboxylic acid
(c) 2-chloro-6-methyl-3-pyridinecarboxylic acid and
(d) 2-chloro-5-methoxy-3-pyridinecarboxylic acid
there are obtained:
(a) 5-bromo-2-chloro-N-(4-hydroxy-1-methyl-4-piperidinylmethyl)-N-methyl-3-pyridinecarboxamide,
(b) 2-chloro-5-methyl-N-(4-hydroxy-1-methyl-4-piperidinylmethyl)-N-methyl-3-pyridinecarboxamide,
(c) 2-chloro-6-methyl-N-(4-hydroxy-1-methyl-4-piperidinylmethyl)-N-methyl-3-pyridinecarboxamide, and
(d) 2-chloro-5-methoxy-N-(4-hydroxy-1-methyl-4-piperidinylmethyl)-N-methyl-3-pyridinecarboxamide.

EXAMPLE 1

1,4'-Dimethylspiro[piperidine-4,2'(3'H)-pyrido[3,2-f]-1,4-oxazepin]-5'(4'H)-one

To a stirred suspension of 6.7 g (0.168 mole) of 60% sodium hydride/mineral oil in 500 ml of dimethylsulfoxide was added 50 g (0.168 mole) of 2-chloro-N-(4-hydroxy-1-methyl-4-piperidinylmethyl)-N-methyl-3-pyridinecarboxamide and the mixture was heated to 70°

C. for 20 hr. An equal volume of dilute sodium hydroxide was added and the solution was extracted twice with methylene chloride. The combined methylene chloride solution was extracted 3 times with water followed by 3 extractions with dilute hydrochloric acid. The acid layers were combined, made basic with concentrated sodium hydroxide, and extracted 3 times with methylene chloride. The combined methylene chloride extract was dried over sodium sulfate and concentrated. Yield of residue was 23 g (52%).

A portion of the residue was recrystallized from isopropyl ether-ethyl acetate, m.p. 109°–111° C.

Analysis: Calculated for $C_{14}H_{19}N_3O_2$: C, 64.35; H, 7.33; N, 16.08; Found: C, 64.40; H, 7.38; N, 16.08.

EXAMPLE 2

1,4'-Dimethylspiro[piperidine-4,2'(3'H)-pyrido[3,2-f]-1,4-oxazepine]-5'(4'H)-thione fumarate [1:1]

To a solution of 11.6 g (0.044 mole) of 1,4'-dimethylspiro[piperidine-4,2'(3'H)-pyrido[3,2-f]-1,4-oxazepin]-5'(4'H)-one in 150 ml of pyridine was added 11.6 g (0.026 mole) of phosphorus pentasulfide and the mixture was heated to reflux for 6 hr. The solution was concentrated on a rotary evaporator (60° C./30 min) and the residue was partitioned between chloroform and dilute sodium hydroxide. The chloroform extract was extracted twice with dilute sodium hydroxide, dried over anhydrous sodium sulfate, and concentrated. The residue was crystallized twice from isopropyl ether-ethyl acetate. Yield of red solid was 8.8 g. The base was dissolved in isopropyl alcohol and treated with 3.8 g of fumaric acid. The resulting solid was recrystallized from ethanol-methanol. Yield of title compound was 8.6 g (55%), m.p. 216°–218° C.

Analysis: Calculated for $C_{18}H_{23}N_3O_5S$: C, 54.95; H, 5.89; N, 10.68; Found: C, 54.77; H, 5.96; N, 10.59.

EXAMPLE 3

Following the general procedure of Example 1 and substituting the following for 2-chloro-N-(4-hydroxy-1-methyl-4-piperidinylmethyl)-N-methyl-3-pyridine carboxamide:

(a) 2-chloro-N-(4-hydroxy-1-ethyl-4-piperidinylmethyl)-N-methyl-3-pyridinecarboxamide,
(b) 2-chloro-N-(4-hydroxy-1-cyclohexyl-4-piperidinylmethyl)-N-methyl-3-pyridinecarboxamide,
(c) 2-chloro-N-(4-hydroxy-1-phenylmethyl-4-piperidinylmethyl)-N-methyl-3-pyridinecarboxamide,
(d) 2-chloro-N-(4-hydroxy-1-phenylethyl-4-piperidinylmethyl)-N-methyl-3-pyridinecarboxamide,
(e) 2-chloro-N-[4-hydroxy-1-(4-methylphenylmethyl)-4-piperidinylmethyl]-N-methyl-3-pyridinecarboxamide,
(f) 2-chloro-N-[4-hydroxy-1-(4-methoxyphenylmethyl)-4-piperidinylmethyl]-N-methyl-3-pyridinecarboxamide,
(g) 2-chloro-N-[4-hydroxy-1-(3,4,5-trimethoxyphenylmethyl)-4-piperidinylmethyl]-N-methyl-3-pyridinecarboxamide,
(h) 2-chloro-N-[4-hydroxy-1-(3-trifluoromethylphenylmethyl)-4-piperidinylmethyl]-N-methyl-3-pyridinecarboxamide,
(i) 2-chloro-N-[4-hydroxy-1-methyl-4-piperidinylmethyl]-N-(phenylmethyl)-3-pyridinecarboxamide,
(j) 2-chloro-N-(4-hydroxy-1-methyl-4-piperidinylmethyl)-N-ethyl-3-pyridinecarboxamide,
(k) 2-chloro-N-(4-hydroxy-1-methyl-4-piperidinylmethyl)-N-(4-chlorophenylmethyl)-3-pyridinecarboxamide,
(l) 2-chloro-N-(4-hydroxy-1-methyl-4-piperidinylmethyl)-N-(4-methylphenylmethyl)-3-pyridinecarboxamide,
(m) 2-chloro-N-(4-hydroxy-1-methyl-4-piperidinylmethyl)-N-(cyclohexylmethyl)-3-pyridinecarboxamide,
(n) 2-chloro-N-(4-hydroxy-1-methyl-4-piperidinylmethyl)-N-isopropyl-3-pyridinecarboxamide, and
(o) 2-chloro-N-(4-hydroxy-1-methyl-4-piperidinylmethyl)-N-cyclohexyl-3-pyridinecarboxamide there are obtained:

(a) 1-ethyl-4'-methylspiro[piperidine-4,2'(3'H)-pyrido[3,2-f]-1,4-oxazepin]-5'(4'H)-one,
(b) 1-cyclohexyl-4'-methylspiro[piperidine-4,2'(3'H)-pyrido[3,2-f]-1,4-oxazepin]-5'(4'H)-one,
(c) 1-phenylmethyl-4'-methylspiro[piperidine-4,2'(3'H)-pyrido[3,2-f]-1,4-oxazepin]-5'(4'H)-one,
(d) 1-phenylethyl-4'-methylspiro[piperidine-4,2'(3'H)-pyrido[3,2-f]-1,4-oxazepin]-5'(4'H)-one,
(e) 1(4-methylphenylmethyl)-4'-methylspiro[piperidine-4,2'(3'H)-pyrido[3,2-f]-1,4-oxazepin]5'(4'H)-one,
(f) 1-(4-methoxyphenylmethyl)-4'-methylspiro[piperidine-4,2'(3'H)-pyrido[3,2-f]-1,4-oxazepin]-5'(4'H)-one,
(g) 1-(3,4,5-trimethoxyphenylmethyl)-4'-methylspiro[piperidine-4,2'(3'H)-pyrido[3,2-f]-1,4-oxazepin]-5'(4'H)-one,
(h) 1-(3-trifluoromethylphenylmethyl)-4'-methylspiro[piperidine-4,2'(3'H)-pyrido[3,2-f]-1,4-oxazepin]-5'(4'H)-one,
(i) 1-methyl-4'-(phenylmethylspiro[piperidine-4,2'(3'H)-pyrido[3,2-f]-1,4-oxazepin]-5'(4'H)-one,
(j) 1-methyl-4'-ethylspiro[piperidine-4,2'(3'H)-pyrido[3,2-f]-1,4-oxazepin]-5'(4'H)-one,
(k) 1-methyl-4'-(4-chlorophenylmethyl)spiro[piperidine-4,2'(3'H)-pyrido[3,2-f]-1,4-oxazepin]5'(4'H)-one,
(l) 1-methyl-4'-(4-methylphenylmethyl)spiro[piperidine-4,2'(3'H)-pyrido[3,2-f]-1,4-oxazepin]-5'(4'H)-one,
(m) 1-methyl-4'-(cyclohexylmethyl)spiro[piperidine-4,2'(3'H)-pyrido-[3,2-f]-1,4-oxazepin]-5'(4'H)-one,
(n) 1-methyl-4'-(isopropyl)spiro[piperidine-4,2'(3'H)-pyrido[3,2-f]-1,4-oxazepin]-5'(4'H)-one, and
(o) 1-methyl-4'(cyclopropyl)spiro[piperidine-4,2'(3'H)-pyrido[3,2-f]-1,4-oxazepin]-5'(4'H)-one.

EXAMPLE 4

Following the general procedure of Example 1 and substituting the following for 2-chloro-N-(4-hydroxy-1-methyl-4-piperidinylmethyl)-N-methyl-3-pyridine carboxamide;

(a) 2-fluoro-N-(4-hydroxy-1methyl-4-piperidinylmethyl)-N-methylbenzamide,
(b) 5-chloro-2-fluoro-N-(4-hydroxy-1-methyl-4-piperidinylmethyl)-N-methylbenzamide,
(c) 4-chloro-2-fluoro-N-(4-hydroxy-1-methyl-4-piperidinylmethyl)-N-methylbenzamide,
(d) 5-bromo-2-fluoro-N-(4-hydroxy-1-methyl-4-piperidinylmethyl)-N-methylbenzamide,
(e) 2-fluoro-5-methyl-N-(4-hydroxy-1-methyl-4-piperidinylmethyl)-N-methylbenzamide, and
(f) 2-fluoro-5-methoxy-N-(4-hydroxy-1-methyl-4-piperidinylmethyl)-N-methylbenzamide there are obtained:

(a) 1,4'-dimethylspiro[piperidine-4,2'(3'H)-[1,4]benzoxazepin-5'(4'H)-one, (b) 7'-chloro-1,4'-dimethylspiro[piperidine-4,2'(3'H)-[1,4]-benzoxazepin]-5'(4'H)-one, (d) 1,4'-dimethyl-7'-methoxyspiro[piperidine-4,2'(3'H)-pyrido[3,2-f]-1,4-oxazepin-5'(4'H)-one.

TABLE 1

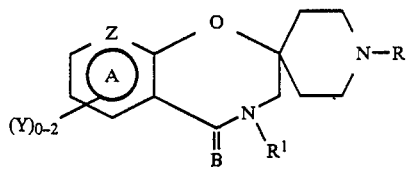

| Example No. | A—(Y)$_{0-2}$ | B | R | R$^1$ |
|---|---|---|---|---|
| 1 | pyrido[3,2-f] | O | —CH$_3$ | —CH$_3$ |
| 2 | pyrido[3,2-f] | S | —CH$_3$ | —CH$_3$ |
| 3(a) | pyrido[3,2-f] | O | —C$_2$H$_5$ | —CH$_3$ |
| (b) | pyrido[3,2-f] | O | —C$_6$H$_{11}$ | —CH$_3$ |
| (c) | pyrido[3,2-f] | O | C$_6$H$_5$CH$_2$— | —CH$_3$ |
| (d) | pyrido[3,2-f] | O | C$_6$H$_5$(CH$_2$)$_2$— | —CH$_3$ |
| (e) | pyrido[3,2-f] | O | 4-CH$_3$—C$_6$H$_4$—CH$_2$— | —CH$_3$ |
| (f) | pyrido[3,2-f] | O | 4-(OCH$_3$)—C$_6$H$_4$—CH$_2$— | —CH$_3$ |
| (g) | pyrido[3,2-f] | O | 3,4,5-(OCH$_3$)$_3$—C$_6$H$_2$—CH$_2$— | —CH$_3$ |
| (h) | pyrido[3,2-f] | O | 3-CF$_3$—C$_6$H$_4$—CH$_2$— | —CH$_3$ |
| (i) | pyrido[3,2-f] | O | —CH$_3$ | C$_6$H$_5$CH$_2$— |
| (j) | pyrido[3,2-f] | O | —CH$_3$ | —C$_2$H$_5$ |
| (k) | pyrido[3,2-f] | O | —CH$_3$ | 4-Cl—C$_6$H$_4$CH$_2$— |
| (l) | pyrido[3,2-f] | O | —CH$_3$ | 4-CH$_3$—C$_6$H$_4$CH$_2$— |
| (m) | pyrido[3,2-f] | O | —CH$_3$ | C$_6$H$_{11}$—CH$_2$— |
| (n) | pyrido[3,2-f] | O | —CH$_3$ | —CH(CH$_3$)$_2$ |
| (o) | pyrido[3,2-f] | O | —CH$_3$ | —C$_6$H$_{11}$ |
| 4(a) | benz | O | —CH$_3$ | —CH$_3$ |
| (b) | 7'-Cl—benz | O | —CH$_3$ | —CH$_3$ |
| (c) | 8'-Cl—benz | O | —CH$_3$ | —CH$_3$ |
| (d) | 7'-Br—benz | O | —CH$_3$ | —CH$_3$ |
| (e) | 7'-CH$_3$—benz | O | —CH$_3$ | —CH$_3$ |
| (f) | 7'-OCH$_3$—benz | O | —CH$_3$ | —CH$_3$ |
| 5(a) | 7'-Br—pyrido[3,2-f] | O | —CH$_3$ | —CH$_3$ |
| (b) | 7'-CH$_3$—pyrido[3,2-f] | O | —CH$_3$ | —CH$_3$ |
| (c) | 8'-CH$_3$—pyrido[3,2-f] | O | —CH$_3$ | —CH$_3$ |
| (d) | 7'-OCH$_3$—pyrido[3,2-f] | O | —CH$_3$ | —CH$_3$ |

(c) 8'-chloro-1,4'-dimethylspiro[piperidine-4,2'(3'H)-[1,4]-benzoxazepin]-5'(4'H)-one, (d) 7'-bromo-1,4'-dimethylspiro[piperidine-4,2'(3'H)-[1,4]-benzoxazepin]-5'(4'H)-one, (e) 1,4',7'-trimethylspiro[piperidine-4,2'(3'H)-[1,4]-benzoxazepin]-5'(4'H)-one, and (f) 1,4'-dimethyl-7'-methoxyspiro[piperidine-4,2'(3'H)[1,4]-benzoxazepin]5'(4'H)-one.

EXAMPLE 5

Following the procedure of Example 1, the following are reacted with sodium hydride:

(a) 5-bromo-2-chloro-N-(4-hydroxy-1-methyl-4-piperidinylmethyl)-N-methyl-3-pyridinecarboxamide, (b) 2-chloro-5-methyl-N-(4-hydroxy-1-methyl-4-piperidinylmethyl)-N-methyl-3-pyridinecarboxamide, (c) 2-chloro-6-methyl-N-(4-hydroxy-1-methyl-4-piperidinylmethyl)-N-methyl-3-pyridinecarboxamide, (d) 2-chloro-5-methoxy-N-(4-hydroxy-1-methyl-4-piperidinylmethyl)-N-methyl-3-pyridinecarboxamide to give the following:

(a) 7'bromo-1,4'-dimethylspiro[piperidine-4,2'(3'H)-pyrido[3,2-f]-1,4-oxazepin-5'(4'H)-one, (b) 1,4',7'-trimehtylspiro[piperidine-4,2'(3'H)-pyrido[3,2-f]-1,4-oxazepin-5'(4'H)-one, (c) 1,4',8'-trimethylspiro[piperidine-4,2'(3'H)-pyrido[3,2-f]-1,4-oxazepin-5'(4'H)-one, and (d) 1,4'-dimethyl-7'-methoxyspiro[piperidine-4,2'(3'H)-pyrido[3,2-f]-1,4-oxazepin-5'(4'H)-one.

PHARMACEUTICAL COMPOSITIONS

The invention further provides pharmaceutical compositions for administration to a living animal body comprising, as active ingredients, at least one of the compounds of Formula I according to the invention in association with a pharmaceutical carrier or excipient. The compounds are thus presented in a therapeutic composition suitable for oral, rectal, parenteral, subcutaneous, intramuscular, intraperitoneal, intravenous, or intranasal administration. Thus, for example, compositions for oral administration can take the form of elixirs, capsules, tblets or coated tablets containing carriers conveniently used in the pharmaeutical art. Suitable carriers or tableting excipients include lactose, potato and maize starches, talc, gelatin and stearic and silicic acids, magnesium stearate and polyvinyl pyrrolidone.

For parenteral administration, the carrier or excipient can be comprised of a sterile parenterally acceptable liquid; e.g., water or arachis oil contained in ampoules.

In compositions for rectal administration, the carrier can be comprised of a suppository base, e.g., cocoa butter or a glyceride.

Application to the nose, throat or bronchial region can be in the form of gargle or an aerosol spray containing small particles of the agent of Formula I in a spray or dry powder form.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed. The exact individual dosages, as well as daily dosages, will of course be determined according to standard medical principles under the direction of a physician or veterinarian. Generally, the pharmacology tests on guinea pigs in comparison to certain other antihistaminic drugs suggests an effective dose for an adult human will be in the range of 1 to 50 mg for the more active compounds.

Based on the animal data, unit dosages containing an amount of compound equivalent to about 0.01 to about 1.0 mg of active drug per kilogram of body weight are contemplated. Daily dosages of about 0.04 to 4.0 mg/kg body weight are contemplated for humans and obviously several small unit dosage forms may be administered at one time. However, the scope of the invention is not to be limited by these contemplations due to uncertainty in transposing from animal data to humans.

Examples of unit dosage compositions are as follows:

| Capsules: | | |
|---|---|---|
| Ingredients | Per Capsule | Per 10,000 Capsules |
| 1. Active ingredient | 4.0 mg | 40 g |
| 2. Lactose | 150.0 mg | 1500 g |
| 3. Magnesium stearate | 4.0 mg | 40 g |
| | 158.0 mg | 1580 g |

Procedure for capsules:
Step 1. Blend ingredient No. 1 and No. 2 in a suitable blender.
Step 2. Pass blend from Step 1 through a No. 30 mesh (0.59 mm) screen.
Step 3. Place screened blend from Step 2 in a suitable blender with ingredient No. 3 and blend until the mixture is lubricated.
Step 4. Fill into No. 1 hard gelatin capsule shells on a capsule machine.

| Tablets: | | |
|---|---|---|
| Ingredients | Per Tablet | Per 10,000 Tablets |
| 1. Active ingredient | 4.0 mg | 40 g |
| 2. Corn starch | 20.0 mg | 200 g |
| 3. Alginic acid | 20.0 mg | 200 g |
| 4. Sodium alginate | 20.0 mg | 200 g |
| 5. Magnesium stearate | 1.3 mg | 13 g |
| | 65.3 mg | 653 g |

Procedure for tablets:
Step 1. Blend ingredients No. 1, No. 2, No. 3, and No. 4 in a suitable mixer/blender.
Step 2. Add sufficient water portionwise to the blend from Step 1 with careful mixing after each addition. Such additions of water and mixing continue until the mass is of a consistency to permit its conversion to wet granules.
Step 3. The wet mass is converted to granules by passing it through an oscillating granulator using a No. 8 mesh (2.38 mm) screen.
Step 4. The wet granules are then dried in an oven at 140° F. until dry.
Step 5. The dry granules are lubricated with ingredient No. 5.
Step 6. The lubricated granules are compressed on a suitable tablet press.

| Intramuscular Injection: | | |
|---|---|---|
| Ingredient | Per ml. | Per liter |
| 1. Active ingredients | 10.0 mg | 10 g |
| 2. Isotonic buffer solution pH 4.0 | q.s. | q.s. |

Procedure:
Step 1. Dissolve the active ingredient in the buffer solution.
Step 2. Aseptically filter the solution from Step 1.
Step 3. The sterile solution is now aseptically filled into sterile ampoules.
Step 4. The ampoules are sealed under aseptic conditions.

| Suppositories: | | |
|---|---|---|
| Ingredients | Per Supp. | Per 1,000 Supp. |
| 1. Active ingredient | 10.0 mg | 10 g |
| 2. Polyethylene Glycol 1000 | 1350.0 mg | 1,350 g |
| 3. Polyethylene Glycol 4000 | 450.0 mg | 450 g |
| | 1810.0 mg | 1,810 g |

Procedure:
Step 1. Melt ingredient No. 2 and No. 3 together and stir until uniform.
Step 2. Dissolve ingredient No. 1 in the molten mass from Step 1 and stir until uniform.
Step 3. Pour the molten mass from Step 2 into suppository molds and chill.
Step 4. Remove the suppositories from molds and wrap.

Therapeutic compositions for combatting histamine in unit dosage form, comprising a pharmaceutical carrier and an effective amount of a compound of Formula I or a pharmaceutically acceptable acid addition salt thereof are therefore an embodiment of this invention.

Various modifications and equivalents will be apparent to one skilled in the art and may be made in the compounds, methods, processes and pharmaceutical compositions of the present invention without departing from the spirit and scope thereof, and it is therefore to be understood that the invention is to be limited only by the scope of the appended claims.

What is claimed is:

1. A compound selected from the group having the formula:

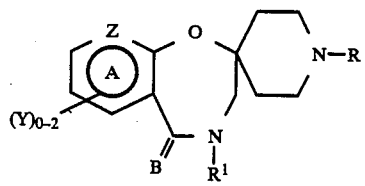

wherein;
A represents an aromatic ring, selected from benzo when Z is carbon or pyrido[3,2-f], when Z is nitrogen, either of which rings may be optionally substituted on carbon by one or two radicals selected from the group consisting of nitro, halo, loweralkyl, loweralkoxy, diloweralkylamino, amino, phenyl or trifluoromethyl;

B is selected from oxygen or sulfur;

$R^1$ is selected from the group consisting of loweralkyl, cycloalkyl, having 3-9 carbon atoms cycloalkyl-loweralkyl wherein the cycloalkyl portion has 3-9 carbon atoms or phenyl-loweralkyl of which phenyl may be optionally substituted by one to three radicals selected from halo, loweralkyl, loweralkoxy, nitro or trifluoromethyl;

R is selected from the group consisting of loweralkyl, cycloalkyl, or phenyl-loweralkyl of which phenyl may be optionally substituted by one to three radicals selected from loweralkyl, loweralkoxy, or trifluoromethyl, and the pharmaceutically acceptable salts thereof.

2. The compound of claim 1 which is 1,4'-dimethylspiro[piperidine-4,2'(3'H)-pyrido[3,2-f]-1,4-oxazepin-5'(4'H)-one or a pharmaceutically acceptable salt thereof.

3. The compound of claim 1 which is 1,4'-dimethylspiro[piperidine-4,2'(3'H)-pyrido[3,2-f]-1,4-oxazepine-5'(4'H)-thione or a pharmaceutically acceptable salt thereof.

4. A compound of claim 1 wherein the aromatic A ring is pyrido[3,2-f] optionally substituted by one or two Y groups.

5. A method of countering histamine in a living animal body which comprises administering to said animal body an effective amount of a compound selected from the group having the formula:

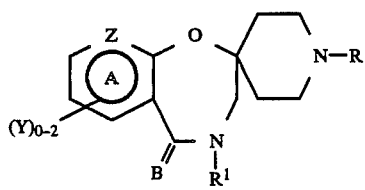

wherein;

A represents an aromatic ring, selected from benzo when Z is carbon or pyrido[3,2-f] when Z is nitrogen, either of which rings may be optionally substituted on carbon by one or two Y radicals selected from the group consisting of nitro, halo, loweralkyl, loweralkoxy, diloweralkylamino, amino, phenyl or trifluoromethyl;

B is selected from oxygen or sulfur;

$R^1$ is selected from the group consisting of loweralkyl, cycloalkyl, having 3-9 carbon atoms cycloalkyl-loweralkyl wherein the cycloalkyl portion has 3-9 carbon atoms or phenyl-loweralkyl of which phenyl may be optionally substituted by one to three radicals selected from halo, loweralkyl, loweralkoxy, nitro or trifluoromethyl;

R is selected from the group consisting of loweralkyl, cycloalkyl, or phenyl-loweralkyl of which phenyl may be optionally substituted by one to three radicals selected from loweralkyl, loweralkoxy, or trifluoromethyl, and the pharmaceutically acceptable salts thereof.

6. The method of claim 5 wherein the compound used is 1,4'-dimethylspiro[piperidine-4,2'(3'H)-pyrido[3,2-f]-1,4-oxazepin-5'(4'H)-one or a pharmaceutically acceptable salt thereof.

7. The method of claim 5 wherein the compound used is 1,4'-dimethylspiro[piperidine-4,2'(3'H)-pyrido[3,2-f]-1,4-oxazepin-5'(4'H)-thione or a pharmaceutically acceptable salt thereof.

8. The method of claim 5 wherein in the compound used, the aromatic A ring is pyrido[3,2-f] optionally substituted for one or two Y groups.

9. A pharmaceutical composition suitable for counteracting histamine comprising:

(a) an effective amount of a compound selected from the group having the formula:

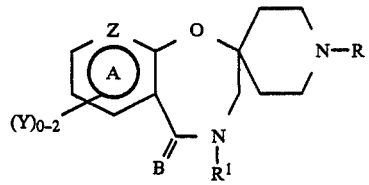

wherein;

A represents an aromatic ring, having two of its carbon atoms held mutually with the oxazepine moiety, selected from benzo when Z is carbon or pyrido[3,2-f], when Z is nitrogen, either of which rings may be optionally substituted on carbon by one or two Y radicals selected from the group consisting of nitro, halo, loweralkyl, loweralkoxy, diloweralkylamino, amino, phenyl or trifluoromethyl;

B is selected from oxygen or sulfur;

$R^1$ is selected from the group consisting of loweralkyl, cycloalkyl, having 3-9 carbon atoms cycloalkyl-loweralkyl wherein the cycloalkyl portion has 3-9 carbon atoms or phenyl-loweralkyl of which phenyl may be optionally substituted by one to three radicals selected from halo, loweralkyl, loweralkoxy, nitro or trifluoromethyl;

R is selected from the group consisting of loweralkyl, cycloalkyl, or phenyl-loweralkyl of which phenyl may be optionally substituted by one to three radicals selected from loweralkyl, loweralkoxy, or trifluoromethyl, and the pharmaceutically acceptable salts thereof and (b) a pharmaceutically acceptable carrier therefor.

10. The pharmaceutical composition of claim 9 wherein the compound used is 1,4'-dimethylspiro[piperidine-4,2'(3'H)-pyrido[3,2-f]-1,4-oxazepin-5'(4'H)-one or a pharmaceutically acceptable salt thereof.

11. The pharmaceutical composition of claim 9 wherein the compound used is 1,4'-dimethylspiro[piperidine-4,2'(3'H)-pyrido[3,2-f]-1,4-oxazepin-5'(4'H)-thione or a pharmaceutically acceptable salt thereof.

12. A pharmaceutical composition of claim 9 wherein in the compound used, the aromatic A ring is pyrido[3,2-f] optionally substituted by one or two Y groups.

* * * * *